(12) United States Patent
Koike et al.

(10) Patent No.: US 7,776,105 B2
(45) Date of Patent: Aug. 17, 2010

(54) HAIR DYE COMPOSITION

(75) Inventors: Kenzo Koike, Tokyo (JP); Yoshinori Saito, Tokyo (JP); Hiroshi Obata, Kyoto (JP); Yukihiro Nakamura, Kyoto (JP); Yoji Hata, Kyoto (JP)

(73) Assignees: Kao Corporation, Tokyo (JP); Gekkeikan Sake Co., Ltd., Kyoto (JP)

( * ) Notice: Subject to any disclaimer, the term of this patent is extended or adjusted under 35 U.S.C. 154(b) by 462 days.

(21) Appl. No.: 11/721,017

(22) PCT Filed: Dec. 6, 2005

(86) PCT No.: PCT/JP2005/022322
§ 371 (c)(1),
(2), (4) Date: Jun. 6, 2007

(87) PCT Pub. No.: WO2006/062070
PCT Pub. Date: Jun. 15, 2006

(65) Prior Publication Data
US 2009/0178209 A1    Jul. 16, 2009

(30) Foreign Application Priority Data
Dec. 8, 2004  (JP) ............................. 2004-355055

(51) Int. Cl.
*A61Q 5/10*   (2006.01)
(52) U.S. Cl. .................. 8/405; 8/406; 8/409; 8/435; 8/611
(58) Field of Classification Search ............ 8/405, 8/406, 409, 435, 611
See application file for complete search history.

(56) References Cited

U.S. PATENT DOCUMENTS

| 5,413,612 A | 5/1995 | Wenke |
| 7,004,980 B2 * | 2/2006 | Saito et al. ............ 8/405 |
| 2003/0150067 A1 * | 8/2003 | Morita et al. .......... 8/405 |

FOREIGN PATENT DOCUMENTS

| JP | 01-233210 A | 9/1989 |
| JP | 03-077813 A | 4/1991 |
| JP | 07-506359 A | 7/1995 |
| JP | A-2001-224381 | 8/2001 |
| JP | 2002-191366 A | 7/2002 |
| JP | A-2002-291496 | 10/2002 |
| JP | A-2003-265177 | 9/2003 |
| JP | 2004-201545 A | 7/2004 |
| WO | WO03/039501 | * 5/2003 |

OTHER PUBLICATIONS

Fujita, Y. et. al., "Molecular cloning and nucleotide sequence of the protyrosinase gene, meIO, from Aspergillus oryzae and expression of the gene in yeast cells," Biochim. Biophys. Acta 1261(1): 151-4 (Mar. 1995), Elsevier Science B.V., The Netherlands.
Dialog File 351, Accession No. 10995900, Derwent World Patents Index, English abstract and patent family for JP 2001-224381, published Aug. 21, 2001.
Dialog File 351, Accession No. 13425173, Derwent World Patents Index, English abstract and patent family for JP 2002-291496, published Oct. 8, 2002.
Dialog File 351, Accession No. 13758509, Derwent World Patents Index, English abstract and patent family for JP 2003-265177, published Sep. 24, 2003.
International Search Report for International Application No. PCT/JP2005/022322, Japanese Patent Office, mailed Mar. 7, 2006.
Patent Abstracts of Japan, abstract of Publication No. JP 01-233210, Hair Dye Composition and Hair-Dyeing Method, published Sep. 19, 1989, (listed on accompanying PTO/SB/08A as document FP1).
Patent Abstracts of Japan, abstract of Publication No. JP 03-077813, Composition for Hair, published Apr. 3, 1991, (listed on accompanying PTO/SB/08A as document FP2).
Patent Abstracts of Japan, abstract of Publication No. JP 2002-191366, New Tyrosinase Gene me1B, published Jul. 9, 2002, (listed on accompanying PTO/SB/08A as document FP4).
Patent Abstracts of Japan, abstract of Publication No. JP 2004-201545, New Tyrosinase Gene meID, published Jul. 22, 2004, (listed on accompanying PTO/SB/08A as document FP5).

* cited by examiner

*Primary Examiner*—Eisa B Elhilo
(74) *Attorney, Agent, or Firm*—Sterne, Kessler, Goldstein & Fox P.L L.C.

(57) ABSTRACT

An air-oxidative type hair dye composition containing a melanin precursor prepared by a process including (A) an oxidation step for converting, into the melanin precursor, a tyrosine or derivative thereof used as a starting substance with an enzyme or cell that is derived from a fungus selected from the group consisting of fungi belonging to the genera *Aspergillus, Neurospora, Rhizomucor, Trichoderma*, and *Penicillium* and that exhibits a catechol oxidase activity.

19 Claims, 1 Drawing Sheet

[Designation of Document]  Drawing
[FIG. 1]
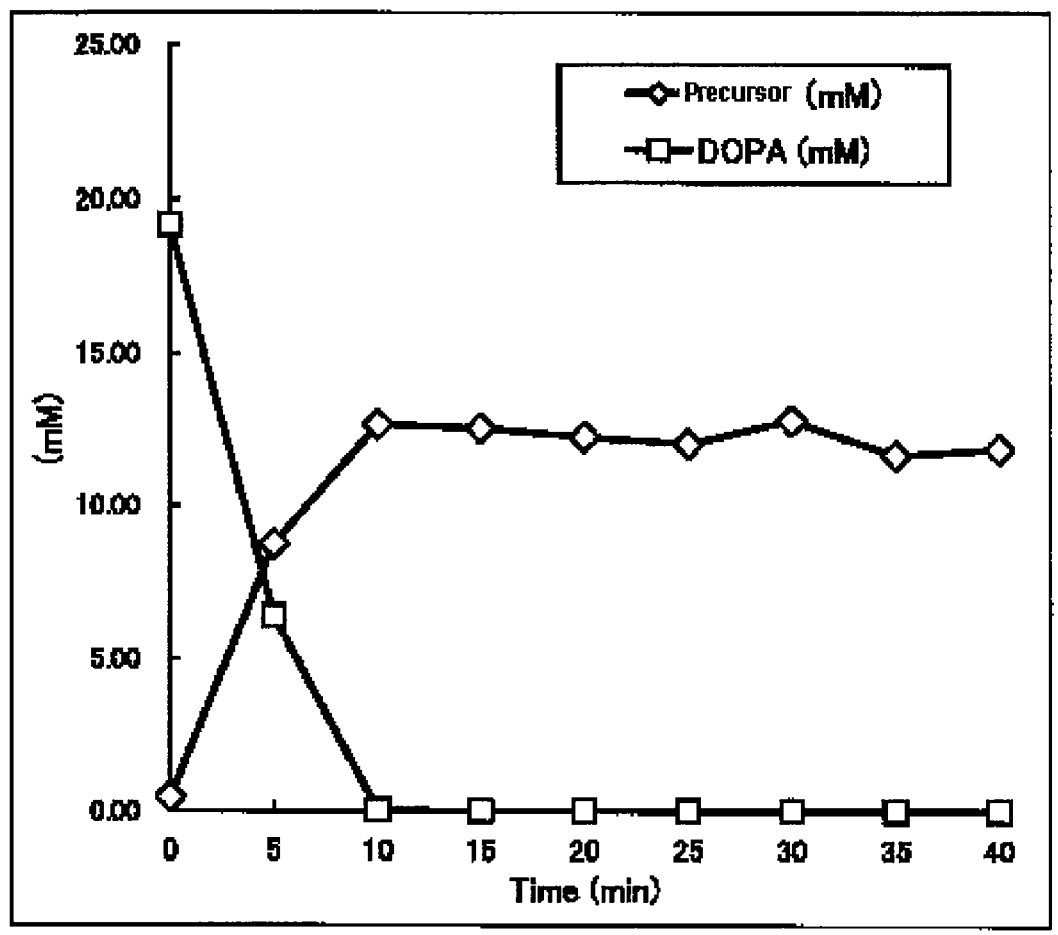

HAIR DYE COMPOSITION

FIELD OF THE INVENTION

The present invention relates to a hair dye composition containing a melanin precursor prepared efficiently by using an enzyme, which has excellent dyeing properties, stability and safety, in particular, a one-part air-oxidative hair dye composition.

BACKGROUND OF THE INVENTION

It is known that melanin precursors such as 5,6-dihydroxyindoline can be converted into melanin pigments by the oxygen in the air. Based on this knowledge, they have been used for air-oxidative hair dyes.

A melanin precursor used for hair dyes can be prepared by a chemical synthesis reaction, but such a preparation process is accompanied by the problems of, for example, reduction in yield due to side reactions, extra time and costs required for the isolation of a target reaction product, and concern about influence of solvent residue. As a preparation technology of a melanin precursor which makes use of an enzymatic reaction, that of an indole or indoline by using laccase is known (Patent Document 1). The laccase used for this reaction however requires purification from plants such as Japanese lacquer, or the like. In addition, the above-described process is not satisfactory because it is inferior in production efficiency and the melanin precursor thus obtained does not have dyeing properties and is not stable.

In Patent Document 2, on the other hand, melB is disclosed as a novel tyrosinase-encoding gene derived from *Aspergillus oryzae*.

[Patent Document 1] JP-A-2002-291496

[Patent Document 2] JP-A-2002-191366

DISCLOSURE OF THE INVENTION

In the present invention, there is provided an air-oxidative type hair dye composition containing a melanin precursor prepared by a process including (A) an oxidation step for converting, into the melanin precursor, a tyrosine or derivative thereof, which is used as a starting substance, with an enzyme or cell derived from a fungus selected from the group consisting of fungi belonging to the genera *Aspergillus, Neurospora, Rhizomucor, Trichoderma,* and *Penicillium* and exhibiting a catechol oxidase activity.

BRIEF DESCRIPTION OF THE DRAWING

FIG. 1 illustrates a change in the concentration of L-DOPA and melanin precursor in the reaction solution obtained during the oxidation of L-DOPA with tyrosinase-producing cells in Preparation Example 1.

MODE FOR CARRYING OUT THE INVENTION

The present invention relates to an air-oxidative hair dye composition which has improved dyeing properties and can be prepared more conveniently by use of, as a dye, a melanin precursor prepared efficiently from a tyrosine or derivative thereof by an enzymatic reaction.

The present inventors have found that an air-oxidative hair dye containing a melanin precursor prepared using an enzyme or an enzyme-containing cell in accordance with a specific process has excellent performances.

The term "melanin precursor" as used in the present invention means a dye which is prepared from a tyrosine or derivative thereof and can be used as an air-oxidative hair dye, that is, a substance which undergoes oxidative polymerization to form melanin immediately when exposed to the oxygen in the air. Specific examples of it include indoline derivatives such as 5,6-dihydroxyindoline and 5,6-dihydroxyindoline-2-carboxylic acid and indole derivatives such as 5,6-dihydroxyindole and 5,6-dihydroxyindole-2-carboxylic acid. DOPA is not embraced within the term "melanin precursor" of the present invention because it is not suited for practical use as a dye for hair dye because of a slow oxidative polymerization rate. Dopachrome, indolequinone and the like are intermediates by oxidative reaction from tyrosine, but since they are stable only for a short period of time and do not have long-term stability (for example, stability for one month), they cannot be used as a dye for hair dye. Accordingly, they are also not embraced within the term "melanin precursor" of the present invention. When a stable compound capable of satisfying the requirements of the above-described air-oxidative hair dye can be prepared from these intermediates by the ordinary chemical treatment or the like, such a stable compound is embraced within the term "melanin precursor" of the present invention. Moreover, the term "melanin precursor" in the present invention is not essentially limited to monomers but it embraces dimers and higher oligomers capable of satisfying the requirements of the above-described air-oxidative dye. The melanin precursor to be used in the present invention is prepared in the below-described process.

Oxidation Step (A)

<Starting Substance>

A tyrosine or derivative thereof is used as the starting substance (substrate compound). Specific examples include (1) D-tyrosine and L-tyrosine, (2) D-DOPA and L-DOPA [DOPA: 3-(3,4-dihydroxyphenyl)alanine), (3) Dopamine (3,4-dihydroxyphenethylamine), (4) lower ($C_{1-4}$) alkyl esters of tyrosines, (5) lower ($C_{1-4}$) alkyl esters of DOPAs, and (6) N-alkoxylated (acetoxylated) or N-alkylated (ethylated) DOPAs, and tyrosines. Isomers of these compounds are also usable. Of these, L-tyrosine and L-DOPA are preferred because a natural type melanin precursor is available therefrom. From the standpoint of affinity to an enzyme, L-DOPA is more preferred. These tyrosines and derivatives thereof may be used either singly or in combination of two or more.

<Enzyme Having a Catechol Oxidase Activity>

The term "catechol oxidase activity" means an activity of catalyzing the oxidation of catechol into o-quinone. Examples of an enzyme having a catechol oxidase activity (which will hereinafter be called "catechol oxidase", simply) include enzymes called catechol oxidase, monophenol oxidase, diphenol oxidase, o-diphenolase and tyrosinase. These enzymes usually have a monophenol oxidase activity. Laccase and peroxidase not having a monophenol oxidase activity but having a polyphenol oxidase activity are also embraced in the enzyme having a catechol oxidase activity. Of these, tyrosinase is preferably used because its high affinity to L-DOPA enables efficient preparation of a natural type melanin precursor. When tyrosine is used as the substrate compound, use of tyrosinase is preferred.

A catechol oxidase may be an enzyme derived from any organism, but tyrosinase derived from fungi is preferred because it has a high expression efficiency and is stable in a host cell. In addition, an enzyme having a high reaction yield (ratio of oxidation product relative to substrate) during a step of oxidation reaction of a tyrosine derivative into a melanin precursor is desired in order to avoid any remains of the starting substance. Examples of such fungi include those belonging to the genera *Aspergillus, Neurospora, Rhizomucor, Trichoderma,* and *Penicillium*. Of these, tyrosinase derived from the fungus of the genus *Aspergillus* is preferred because it has relatively high heat stability and in addition, its safety has already been confirmed. Specific examples of it include enzymes substantially the same as tyrosinase which is coded by genes melB (JP-A-2002-191366), melD (JP-A-2004-201545) and melO (Molecular cloning and nucleotide sequence of the protyrosinase gene, melO, from *Aspergillus oryzae* and expression of the gene in yeast cells, *Biochim Biophys Acta.,* Mar. 14, 1261 (1): 151-154 (1995)), each from *Aspergillus oryzae*.

In the present invention, the term "substantially the same" as the above-described genes (melB gene, melD gene and melO gene) means that the enzyme has at least 70%, more preferably at least 80%, even more preferably at least 90% homology, in amino acid sequence, with at least any one of these genes and at the same time has a tyrosinase activity or monophenol oxidase activity. Use of such an enzyme provides a high reaction yield of Dopachrome from DOPA, enables efficient oxidation reaction and contributes to a reduction in the final DOPA concentration in the oxidation step.

The above-described enzyme can be added to a reaction solution as is. Alternatively, it may be added in the form of an immobilized enzyme from the viewpoints of improvement of the stability of the enzyme, ease of isolation after use and avoidance of protein incorporation in the reaction system. No particular limitation is imposed on the immobilizing method of the enzyme and examples of it include known methods such as crosslinking between enzyme molecules through an immobilization support and encapsulation of the enzyme in a gel such as alginate gel. The enzyme may be either a crude preparation containing foreign substances derived from organisms or a purified enzyme, but when it is used as an immobilized enzyme, it is preferably a purified one.

<Cell Exhibiting a Catechol Oxidase Activity>

A cell corresponding to at least one of the following (a) to (d) is used as the cell exhibiting a catechol oxidase activity.

(a) A cell that expresses a gene encoding a polypeptide having a catechol oxidase activity under the control of a promoter more active than another promoter under the control of which the gene is originally expressed.

(b) A cell having a plurality of copies of a gene encoding a polypeptide having a catechol oxidase activity.

(c) A cell exhibiting a higher catechol oxidase activity by having a mutated gene encoding a polypeptide having a catechol oxidase activity.

(d) A cell exhibiting an increased catechol oxidase activity by tyrosinase activation treatment.

With regard to (a), a large amount of a catechol oxidase can be produced, for example, by introducing a vector ordinarily employed for the abundant expression of protein into which catechol oxidase gene has been cloned, into a host cell to implant it in a host chromosome or cultivating the host cell having it in the form of a plasmid. By the above-described method, the gene can be expressed under the control of a promoter more active than another promoter under the control of which the gene is originally expressed.

With regard to (b), a diploid or greater cell having a possibility of retaining two or more copies of a catechol oxidase gene into which the catechol oxidase gene has been introduced may be used. There are triploid or tetraploid cells, for example, in some industrial yeasts, and they are also preferred. By increasing the copy number of a gene than the original number, a cell exhibiting a high catechol oxidase activity is available.

With regard to (c), a cell whose catechol oxidase activity has been enhanced by the mutation of a catechol oxidase gene or cell having such a mutated catechol oxidase gene introduced thereinto can be used. The cell can exhibit a higher catechol oxidase activity by the conversion into a mutated enzyme exhibiting a higher activity than a naturally occurring enzyme.

With regard to (d), a cell whose catechol oxidase activity has been enhanced by the coordination of a divalent copper ion or treatment with an acidic solution having a pH of from about 2.8 to 3.2 can also be used.

Of these, the cell (a) that expresses a gene encoding a polypeptide having a catechol oxidase activity under the control of a promoter more active than another promoter under the control of which the gene is originally expressed is preferred.

The kind of a catechol-oxidase producing cell is not particularly limited, but a microorganism is preferred because it can be easily cultivated in a large quantity. Examples of the microorganism which can be handled easily include *Escherichia coli*, yeasts and fungi. Of these, yeasts are preferred because they are safe, can efficiently produce a catechol oxidase, are single-cell organisms, and can be centrifugally separated at a relatively low rotation speed after reaction because of a high precipitation rate of the cell. Of the yeasts, *Saccharomyces cerevisiae* is preferred because the cellular body is tough enough to prevent the protein derived from the cell from flowing into the reaction solution and its gene can be manipulated easily.

It is also possible to use a cell immobilized by a known method such as a carrier binding method, entrapping method, crosslinking method and photo-crosslinking method from the standpoints of efficient use and ease of isolation after use.

<Activation Treatment>

Catechol oxidases such as tyrosinase need coordination of a divalent copper ion in the catalyst active center so as to exhibit its activity. A wild type cell exhibits sufficient activity owing to the coordination of a divalent copper ion present in the cell because an expression level of catechol oxidase is small. Some cells cannot exhibit a sufficient catechol oxidase activity when they have an improved expression level of catechol oxidase by the transformation or the like. In either case whether the enzyme or cell exhibiting a catechol oxidase activity is employed, it is preferred to coordinate a divalent copper ion in the catalyst active center of catechol oxidase by treating the enzyme or cell with a divalent copper ion in advance. Described specifically, it is preferred to sufficiently coordinate a divalent copper ion in catechol oxidase within the cell by suspending the enzyme or transformant thereof in a copper sulfate solution of from about 0.1 to 2 mM or the like and allowing the resulting solution to stand at from about 30 to 40° C. for from about 0.5 to 2 hours.

Of catechol oxidases, tyrosinase, especially tyrosinase derived from *Aspergillus oryzae* matures and activates by treating it with an acid solution having a pH of from about 2.8 to 3.2. Irrespective of whether the enzyme or cell exhibiting a catechol oxidase activity is employed, therefore, it is preferred to improve the catechol oxidase activity further by suspending it in a sodium acetate buffer solution (pH=3) of from about 20 to 200 mM and allowing the resulting suspension to stand for from about 0.5 to 1 hour at from about 0 to 40° C.

The catechol oxidase can also be activated by the treatment with a protease such as an endopeptidase, which selectively breaks down a specific peptide bond, such as trypsin. When it is treated with the protease, an N-terminal and/or C-terminal sequence of the enzyme is eliminated, leading to improvement of an enzymatic activity.

When the cell exhibiting a catechol oxidase activity is a yeast cell and L-DOPA is employed as the substrate, the cell has a catechol oxidase activity of preferably 0.1 U/OD$_{600}$ or greater, more preferably 0.5 U/OD$_{600}$ or greater, even more preferably 1 U/OD$_{600}$ or greater. Even when the cell is other than a yeast cell, it has preferably an equal level of a catechol oxidase activity. Although the upper limit of the catechol oxidase activity of the cell is not particularly limited, it is usually about 5 U/OD$_{600}$.

Irrespective of whether the enzyme or cell exhibiting a catechol oxidase activity is employed, the catechol oxidase activity thereof is usually adjusted to $5 \times 10^5$ U/mol or greater, preferably $5 \times 10^6$ U/mol or greater when 1 mole of L-DOPA is employed as the substrate. Although the upper limit of a catechol oxidase activity per mole of L-DOPA is not particularly limited, about $5 \times 10^7$ U/mol is usually sufficient and activities exceeding it lead to a high cost.

In the present invention, a catechol oxidase activity (U/OD$_{600}$) of the enzyme or cell is determined by assuming that the activity required for increasing, by 1, the absorbance at 475 nm of a reaction solution obtained by reacting 1 mL of a solution containing the enzyme or cell and 0.8 μmol of DOPA at 30° C. for 5 minutes is 1 U and dividing it by the density of the cell employed for the reaction (absorbance at 600 nm: OD$_{600}$).

In the process of the present invention, owing to the presence of the catechol oxidase in excess relative to the substrate, a preparation rate of a melanin precursor from the substrate compound is higher than that of melanin formed as a result of polymerization of the melanin precursor prepared from the substrate compound, whereby the melanin precursor accumulates efficiently in the reaction system.

<Reaction>

It is preferred to adjust the concentration of the starting substance (substrate compound) upon initiation of the reaction to usually from about 10 to 60 mM, more preferably from about 15 to 25 mM. The concentration of the starting substance within the above-described range enables preparation of a sufficient amount of the melanin precursor and at the same time, causes neither a reduction in the yield of the melanin precursor nor the remains of the unreacted substrate, which will otherwise occur by an excessive increase in the preparation amount of melanin. Use of DOPA, Dopamine or the like as the starting substance is not preferred because it is not suited as a raw material of a hair dye from the viewpoint of safety. It is therefore preferred to consume DOPA or Dopamine which is a starting substance or intermediate during the oxidation step in order to avoid the substantial incorporation of it in a hair dye. It is more preferred to use L-DOPA as the starting substance and carry out the oxidation step while adjusting the concentration of the starting substance to 15 mM or greater upon initiation of the reaction and to 0.1 mM or less upon completion of the reaction. In addition, it is economical and therefore preferred to adjust the yield of the oxidation product such as Dopachrome obtained as a result of the enzymatic reaction of DOPA to fall within a range of from about 30 to 70%.

The pH of the reaction solution may fall within a range where the enzyme can catalyze the oxidation reaction of the substrate, but it is preferred to keep the pH usually to from about 4 to 9, more preferably from about 5 to 7 in order to suppress the preparation of melanin and efficiently accumulate the melanin precursor in the reaction solution. The pH of the reaction solution can be kept within the above-described range by using a buffer as the reaction solution, but the preparation of melanin is sometimes accelerated by the polymerization of the melanin precursor at a high salt concentration. It is therefore preferred to adjust the pH by adding a small amount of a strong alkali such as potassium hydroxide or sodium hydroxide or a strong acid such as sulfuric acid or hydrochloric acid.

From the viewpoints of facilitating the cell isolation after the reaction and improving the production yield of the melanin precursor, the amount of the cell in the reaction solution is preferably smaller while keeping the catechol oxidase activity within the above-described range. The charged amount of the cell is preferably 20 vol. % or less, more preferably 10 vol. % or less based on the amount of the reaction solution.

The reaction temperature may fall within a range where the enzyme can catalyze the oxidation reaction of the substrate, but it is preferred to keep the temperature at from 5 to 40° C., more preferably from 15 to 35° C., even more preferably from 20 to 30° C. from the viewpoints of sufficient progress of the oxidation reaction, prevention of deactivation of the enzyme and prevention of melanization.

Immediately after the reaction is started, the oxidation reaction needs a large amount of oxygen so that it is preferred to stir the reaction solution to vigorously aerate it. A too high stirring speed may cause damage to the cell or the like so that it is preferred to monitor the oxygen concentration in the reaction solution and reduce the air flow quantity and stirring speed when a decrease in the oxygen concentration is terminated. The oxygen concentration in the reaction solution is preferably kept at from about 0.1 to 8 ppm, more preferably from about 1 to 2 ppm. When much foam appears in the reaction solution by aeration or stirring of the reaction solution, a defoaming agent such as silicone resin may be added.

The reaction may be performed either by the batch system or the continuous system, but the former one is preferred because it can separate the unreacted substrate from the product. The reaction time in the batch system is usually from about 10 minutes to 2 hours, more preferably from about 30 minutes to 1 hour in order to sufficiently convert the substrate compound into a melanin precursor while suppressing the polymerization reaction of the melanin precursor to the minimum.

In the continuous system, on the other hand, the reaction solution may be collected continuously while supplying a cell-containing reaction vessel with the substrate to give a substrate concentration of from about 10 to 60 mM, more preferably from about 15 to 25 mM. Alternatively, to a column charged with a support on which the enzyme or cell has been immobilized, the substrate may be added to give a concentration of from about 1 to 10 mM, more preferably from about 3 to 6 mM and hydrogen peroxide twice the concentration of the substrate may be added as an electron donor.

When tyrosine or DOPA is used as the substrate compound, the substrate compound is oxidized into Dopachrome by the above-described enzymatic reaction. When the reaction is terminated and reduced by using a reducing agent such as ascorbic acid or dithionous acid, 5,6-dihydroxyindoline-2-carboxylic acid can be obtained as a melanin precursor. When the reaction solution is maintained further, 5,6-dihydroxyindole is prepared by the voluntary decarboxylation of Dopachrome, or 5,6-dihydroxyindole-2-carboxylic acid is prepared from Dopachrome by Dopachrome tautomerase contained in the cell or by the non-enzymatic isomerization. As a result, a melanin precursor composed of Dopachrome, 5,6-dihydroxyindole, and 5,6-dihydroxyindole-2-carboxylic acid can be obtained. The reaction yield of the melanin precursor is preferably from 20 to 70%, more preferably from 40 to 70%.

When Dopamine is used, for example, as the substrate compound, the substrate compound is oxidized into a quinone derivative of Dopamine. When the reaction is terminated and reduced by using a reducing agent such as dithionous acid, 5,6-dihydroxyindoline can be obtained. When the reaction solution is maintained further, dihydroxyindole is formed. The melanin precursor sometimes may include a water soluble oligomer obtained by the polymerization of from about 2 to 5 molecules thereof.

The melanin precursor can be prepared by using a DOPA ester or a tyrosine ester as the starting substance. When an alkyl ester is employed as the substrate compound, a melanin precursor that produces melanin having a color other than black can be prepared. As a specific example, when a tyrosine ethyl ester or DOPA ethyl ester is used as the starting substance, melanin obtained by the polymerization of the resulting melanin precursor becomes yellow and therefore it can be used for toning of a hair dye.

Post-Treatment Step (B)

The oxidation step (A) for the preparation of a melanin precursor to be used for the hair dye of the present invention is the above-described reaction by the enzyme or a cell. A post-treatment step (B) for making the melanin precursor suited for use in the hair dye will next be described.

(1) Collection of a Melanin Precursor

The reaction solution containing the melanin precursor obtained by the oxidation step (A) contains, in addition to it, the enzyme or cell used for the reaction, protein produced as a result of the breakage of the cell by aeration and stirring, protein leaked from the cell, and melanin formed by the polymerization of the melanin precursor. In order to utilize the reaction solution for a dye for hair dye, they need to be removed from the reaction solution. The enzyme or cell can be removed by ultrafiltration, filtration, centrifugal separation or the like means. The enzyme or cell thus collected is returned for reuse to the container for the oxidation step. The protein or melanin can be removed by ultrafiltration, gel filtration chromatography or the like means.

The melanin precursor obtained in the oxidation step (A) is a substance that will be a polymer (melanin) having a molecular weight of 3000 or greater, more specifically, it is in the form of a monomer or oligomer having an indole or indoline skeleton (having a molecular weight less than 3000) and mainly contains Dopachrome or 5,6-dihydroxyindoline-2-carboxylic acid. In the present invention, the air-oxidative hair dye composition may be prepared by incorporating the crude melanin precursor as a dye.

It is also possible to carry out oxidative polymerization of the melanin precursor obtained in the oxidation step of the present invention into melanin having only a molecular weight of 3000 or greater and incorporate it in a hair cosmetic composition (leave-on or rinse-off type). Examples of the composition include shampoo, rinse, conditioner, hair styling product, hair setting product, permanent wave solution, wax, hair gloss product, and hair growth enhancer.

(2) Control of Melanin Precursor Composition

In the present invention, the melanin precursor solution is preferably incorporated in a hair dye after the below-described step [Step (I)] of increasing, depending on the purpose of use, the concentration of either 5,6-dihydroxyindole or 5,6-dihydroxyindole-2-carboxylic acid in the melanin precursor solution. This step may be performed either before or after the above-described collection step (removal of enzyme, cell, protein, melanin and the like from the reaction solution). In order to perform these steps simultaneously, it is also possible to perform the collection step under the environment of the below-described step (I) to include the time of the collection step in the time of the step (I). It is preferred to increase the concentration of 5,6-dihydroxyindole or 5,6-dihydroxyindole-2-carboxylic acid and after this step, incorporate the melanin precursor solution in a hair dye. In the more preferred embodiment, the melanin precursor solution contains 5,6-dihydroxyindole as a main component and, with respect thereto, a small amount of 5,6-dihydroxyindole-2-carboxylic acid. A hair dye containing such a precursor solution can dye the hair with a more natural color.

Examples of a method for increasing the concentration of either one of the compounds in the step (I) include (i) pH adjustment, (ii) addition of a water-soluble organic solvent, (iii) addition of an inorganic salt, (iv) treatment with a buffer, and (v) addition of an antioxidant. These methods may be used either singly or in combination of two or more. For example, this step can be completed more efficiently by carrying out one or more of the methods (ii) to (v) during the pH adjustment (i).

(i) Adjustment of pH

The pH is adjusted to preferably from 5 to 11, more preferably from 5 to 10, even more preferably from 6 to 9. Within this range, conversion into an indole derivative proceeds efficiently. On the other hand, precipitation occurs at a strongly acidic pH, while acceleration of oxidative polymerization results in the appearance of melanin at a strongly alkaline pH. This pH adjustment is performed preferably under anaerobic conditions, but a presence of oxygen is not always denied if the compound can be yielded sufficiently in the step (I).

In this treatment, it is possible to control the composition of the melanin precursor to increase the ratio of a desired compound by adjusting the pH to from neutral to weakly acidic or to alkaline. For example, conversion from Dopachrome or 5,6-dihydroxyindoline-2-carboxylic acid to 5,6-dihydroxyindole tends to occur at a pH of 5 or greater but less than 8 and conversion from 5,6-dihydroxyindoline-2-carboxylic acid to 5,6-dihydroxyindole-2-carboxylic acid tends to occur at a pH of 8 or greater but not greater than 11. This means that 5,6-dihydroxyindole is formed in a neutral to acidic region, while 5,6-dihydroxyindole-2-carboxylic acid is formed efficiently in an alkaline region.

The temperature during the pH adjustment is preferably from 5 to 40° C., more preferably from 15 to 30° C. It is therefore preferred to perform pH adjustment usually at room temperature. The pH adjustment is continued preferably for a period of time, with the time required for the conversion of a 5,6-dihydroxyindoline derivative as an index. The time may be 30 minutes or greater, though depending on the temperature. Since the conversion product (5,6-dihydroxyindole derivative) is relatively stable, no problem occurs even if it is left to stand for a long period of time, for example, 1 week or more if oxygen is blocked.

(ii) Addition of Water-Soluble Organic Solvent

As the water-soluble organic solvent, an organic solvent having compatibility of 10 wt. % or greater in water (this means that 10 g or greater of the solvent dissolves in 90 g of water) can be used. Examples of the water-soluble organic solvent usable here include alcohols such as methanol, ethanol, and benzyl alcohol, polyols such as polyethylene glycol and glycerin, ketones such as acetone, organic acids such as lactic acid and citric acid, fatty acids such as acetic acid and propionic acid, alkylamines and alkanolamines such as monoethanolamine. Of these, ethanol and acetone are more preferred from the standpoint of safety.

In particular, the addition of an alcohol, polyol, ketone, organic acid or fatty acid accelerates the conversion of 5,6-dihydroxyindoline-2-carboxylic acid into 5,6-dihydroxyindole. For example, when ethanol is added in an amount of 50 wt. %, the conversion speed of 5,6-dihydroxyindoline-2-carboxylic acid into 5,6-dihydroxyindole increases to about 2 times. Addition of the alkylamine or alkanolamine can accelerate the conversion of 5,6-dihydroxyindoline-2-carboxylic acid to 5,6-dihydroxyindole-2-carboxylic acid. For example, addition of monoethanolamine in an amount of from 5 to 50 wt. % enables conversion of 5,6-dihydroxyindoline-2-carboxylic acid into 5,6-dihydroxyindole-2-carboxylic acid at a selectivity of 70% or greater.

The water-soluble organic solvent is preferably added to the reaction solution to give a concentration of from about 5 to 70 wt. %, more preferably from about 30 to 60 wt. % in the whole amount. The amount of the solvent exceeding the above-described range does not cause any particular problem, but on the contrary, it is effective for increasing the conversion speed and removing the inevitably produced melanin. Amounts within the above-described range however enable improvement of a ratio of the 5,6-dihydroxyindole derivative sufficiently to be suited for practical use and at the same time, enable safe post treatment.

(iii) Addition of Inorganic Salt

As the inorganic salt, alkali metal salts, alkaline earth metal salts and copper (II) salts of an acid selected from hydrochloric acid, nitric acid, sulfuric acid and carbonic acid can be employed. of these, the copper (II) salts can accelerate the conversion of 5,6-dihydroxyindoline-2-carboxylic acid into 5,6-dihydroxyindole-2-carboxylic acid, while inorganic salts other than the copper (II) salts can accelerate the conversion of 5,6-dihydroxyindoline-2-carboxylic acid into 5,6-dihydroxyindole. The concentration of the inorganic salt in the reaction solution is preferably 40 wt. % or less, more preferably from 0.1 to 20 wt. % or less, even more preferably from 1 to 5 wt. % from the viewpoints of conversion efficiency and prevention of the precipitation of the salt or melanin.

When copper sulfate, for example, is used as the inorganic salt, it is added to give a concentration of from about 0.1 to 20 mM, preferably from 5 to 10 mM. The resulting mixture is stored, for example, for about 10 to 30 minutes, whereby the conversion of 5,6-dihydroxyindoline-2-carboxylic acid into 5,6-dihydroxyindole-2-carboxylic acid in the melanin precursor is accelerated.

(iv) Treatment with Buffer

As the buffer, a phosphate buffer can be used. Examples of the phosphate buffer include sodium phosphate buffer, potassium phosphate buffer, citric acid-sodium phosphate buffer, and Tris-phosphate buffer. Treatment with the phosphate buffer makes it possible to accelerate the conversion of 5,6-dihydroxyindoline-2-carboxylic acid into 5,6-dihydroxyindole-2-carboxylic acid.

(v) Addition of Antioxidant

As the antioxidant, ascorbic acid, sodium ascorbate, sodium sulfite and the like can be used. Addition of 2.5 wt. % of sodium ascorbate can increase the conversion speed of 5,6-dihydroxyindoline-2-carboxylic acid into 5,6-dihydroxyindole.

(3) Concentration and Storage of the Melanin Precursor

It is preferred to remove water from the melanin precursor solution containing the melanin precursor, thereby concentrating the solution in a known manner such as reverse osmotic concentration, spray drying, or freeze concentration. The melanin precursor, whether it is a single melanin precursor component or a mixture thereof, may be stored in any form such as a concentrate or dry powder.

A description will next be made of the storing method of a specific melanin precursor component. An indoline derivative such as 5,6-dihydroxyindoline or 5,6-dihydroxyindoline-2-carboxylic acid is stored preferably in the form of a powdery salt (preferably, hydrochloride, bromate or the like), preferably in the absence of oxygen. An indole derivative such as 5,6-dihydroxyindole or 5,6-dihydroxyindole-2-carboxylic acid can be stored in the solution or powdery form in the substantial absence of oxygen.

The indoline derivative such as 5,6-dihydroxyindoline or 5,6-dihydroxyindoline-2-carboxylic acid is stored preferably in the absence of oxygen while being blocked from water (including the form of powder or suspension in an oil) until it is used as a hair dye component. It is mixed with an ordinarily employed base of a hair dye such as water and alkali agent immediately before use, and without pause, the mixture is applied to the hair as a hair dye. In this case, from the standpoint of the stability of the melanin precursor, the hair dye is preferably a two-part or three-part type which needs a mixing operation or the like, though it is an air-oxidative hair dye.

The indole derivative such as 5,6-dihydroxyindole or 5,6-dihydroxyindole-2-carboxylic acid is, on the other hand, stable in an aqueous solution in the absence of oxygen so that it can be used for a one-part air-oxidative hair dye. It is preferred because it can be used conveniently. From the standpoints of ease of preparation, stability and hair dyeing performance, 5,6-dihydroxyindole is preferred and a percentage of 5,6-dihydroxyindole in the melanin precursor is preferably 60% or greater in terms of an area ratio of an absorbance at 280 nm. On the other hand, 5,6-dihydroxyindole-2-carboxylic acid is suitably added to a hair dye composition for temporary dyeing because melanin obtained by the polymerization of it has high water solubility.

Hair Dye Composition

Incorporation of the melanin precursor obtained in the above-described manner makes it possible to provide a one-part air-oxidative hair dye that can dye the hair easily only by taking it out from the container, applying it to the hair and leaving the resulting hair for a while. Silver hair can be dyed into a natural color attributable to melanin. Among the melanin precursor components, 5,6-dihydroxyindole is suited for the preparation of a one-part hair dye. If the hair dye can exhibit hair dyeing performance fully, however, another melanin precursor component may be added in an amount up to about half of the total melanin precursor amount.

The content of the melanin precursor in the hair dye composition of the present invention is preferably from 0.01 to 10 wt. %, more preferably from 0.05 to 5 wt. %, even more preferably from 0.1 to 1 wt. % from the standpoint of the hair dyeing performance. The content of the melanin precursor can be changed as needed, depending on the purpose of use of the hair dye. When the hair is dyed to a desirable dark (black) color by single dyeing, the content is preferably from about 0.5 to 1 wt. %. When the hair is repeatedly dyed little by little making the silver hair less noticeable, the hair dye has a melanin precursor content of preferably from 0.1 to 0.4 wt. %. A hair dye containing the melanin precursor in an amount of 0.01 wt. % or greater can dye the hair, though little by little so that it can be used for a hair dye to be applied by the hands, a dye for color rinse, or a hair cosmetic composition.

The preparation process of the melanin precursor to be used in the present invention utilizes an enzymatic reaction similar to that in vivo so that it has an advantage of not requiring a complex purification operation for removing the by-products which will otherwise appear as a result of the chemical reaction using a catalyst. Since the melanin precursor contains almost no by-products other than the melanin-related substances and in addition, it is similar to a melanin precursor present in nature, it is expected to bring about excellent effects from the viewpoint of safety compared with oxidation dyes prepared by other chemical synthesis or conventional processes.

The hair dye composition of the present invention is adjusted to preferably from pH 6 to 11, more preferably from pH 7 to 10.5. For the pH adjustment, alkali agents such as sodium hydroxide, potassium hydroxide, ammonia, guanidine, alkylamines, basic amino acids, and carbonate salts may be employed. Specific examples of the alkylamines include monoethanolamine; those of the basic amino acids include arginine, lysine, and histidine; and those of the carbonate salts include sodium carbonate, potassium carbonate, guanidine carbonate, and sodium bicarbonate. In combination with the alkali agent, an inorganic or organic acid such as hydrochloric acid, sulfuric acid, phosphoric acid, citric acid or lactic acid can also be used as needed. These pH regulators may be used in combination of two or more. The content of the pH regulator is preferably from 0.01 to 20 wt. %, more preferably from 0.1 to 10 wt. % based on the whole composition.

A water compatible organic solvent may be contained as a complementary component of the hair dye. Examples of the water compatible organic solvent include lower alcohols such as ethanol and propanol, glycols such as ethylene glycol and propylene glycol, ethylene glycol monoethers such as ethylene glycol monomethyl ether, ethylene glycol monoethyl ether and ethylene glycol monobutyl ether; carbitols such as diethylene glycol monoethyl ether and diethylene glycol monobutyl ether; benzyloxyethanol and benzyl alcohol. Of these, the lower alcohols and glycols are preferred. These water compatible organic solvents may be used in combination of two or more. In particular, when benzyloxyethanol or benzyl alcohol is used, it is preferably used in combination with another solvent, especially, a lower alcohol or glycol. The content of the water compatible organic solvent is preferably from 5 to 50 wt. %, more preferably from 10 to 40 wt. %, even more preferably from 15 to 30 wt. % based on the whole composition, from the viewpoint of the dyeing properties.

To the hair dye of the present invention, an amino acid (especially, cysteine) or a conventional oxidation dye or direct dye (acid dye, basic dye or dissociation dye) may be added as a toning component. The content thereof is preferably from 0.001 to 5 wt. %, more preferably from 0.01 to 2 wt. %, even more preferably from 0.05 to 1 wt. %, though depending on the purpose of use.

The hair dye composition of the present invention can be provided in the form such as cream, gel, lotion or foam by controlling the viscosity of the composition by adding a thickener thereto. Examples of the thickener include cellulose derivatives such as hydroxyethyl cellulose, ether between hydroxyethyl cellulose and glycidyl trimethylammonium chloride, methyl cellulose and carboxymethyl cellulose; natural gums such as xanthan gum and guar gum; and synthetic polymers such as polyvinylpyrrolidone, crosslinked polyacrylic acid or salt thereof, polyacrylic acid or salt thereof, and polyacrylamide. The kind and amount of the thickener can be determined depending on the desired viscosity and the viscosity of the hair dye composition is preferably from 100 to 50000 mpa·s. The hair dye composition of the present invention provides a light feeling upon use when it is not thickened, but the composition having a viscosity increased by the addition of the thickener can be used without losing the dyeing power and without fear of dripping.

The hair dye composition of the present invention can contain a foaming agent and/or a nonionic surfactant as a homogenizing agent. Examples of the nonionic surfactant include polyoxyethylene alkyl ethers such as polyoxyethylene oleyl ether and polyoxyethylene stearyl ether; polyoxyethylene alkylphenyl ethers such as polyoxyethylene nonylphenyl ether and polyoxyethylene octylphenyl ether; polyoxyethylene sorbitan fatty acid esters, fatty acid alkylolamides, and polyoxyethylene-sec-tetradecyl ether. The content of the nonionic surfactant is preferably from 0.01 to 30 wt. %, more preferably from 0.1 to 10 wt. %.

Addition of an antioxidant to the hair dye composition of the present invention is desired in order to ensure stability. Examples of the antioxidant include ascorbic acids such as ascorbic acid, sodium ascorbate, and ascorbate esters, inorganic salts such as sodium sulfite, cysteine derivatives such as cysteine and N-acetylcysteine, plant extracts exhibiting antioxidant action such as rosemary extract and tea extract, vitamins such as tocopherol and tocopherol acetate, and scavengers such as BHT. Of these, ascorbic acids are preferred and in view of the pH of the composition when it is applied, sodium ascorbate is preferred. In addition, a chelating agent such as EDTA or salt thereof, or 1-hydroxyethane-1,1-diphosphonic acid or salt thereof may be used as a component for improving the stability.

In addition to the above-described components, the hair dye composition of the present invention may contain components conventionally employed for hair dyes such as surfactants, stabilizers, buffers, perfumes, feel improvers, chelating agents, solubilizing agents, and antiseptics, all of which are other than the above-described ones, as needed, depending on the purpose of use.

A gradually dyeing type hair dye that is used in repetition is a preferred mode of the hair dye composition of the present invention. In addition, it is preferably in the aerosol form.

The hair dye composition of the present invention in the aerosol form may be prepared by filling both the hair dye composition and a propellant in a pressure bottle (aerosol can or the like). As the propellant, a compressed gas, liquefied gas, or the like which is ordinarily employed in aerosol products can be used. Examples of the compressed gas include nitrogen gas, carbonic acid gas and argon gas, while those of the liquefied gas include liquefied petroleum gas, lower saturated hydrocarbons and dimethyl ether. Two or more of these propellants may be used in combination. It is preferred to add the propellant(s) in an amount of from 1 to 20 wt. %, more preferably from 3 to 15 wt. % in the whole composition in order to inject the composition at an adequate velocity. In addition, the internal pressure of the aerosol can after filling is controlled preferably to from 3 to 5 kg/cm$^2$G (25° C.).

It is also possible to add melanin, which has been obtained by the oxidative polymerization of the melanin precursor obtained in the oxidation step of the present invention, to a hair cosmetic composition (leave-on type or rinse-off type) as melanin having only a molecular weight of 3000 or greater. Examples of the hair cosmetic composition include shampoos, rinses, conditioners, styling products, hair setting products, permanent wave products, waxes, luster enhancing agents, and hair growth enhancers. The form of the composition is, for example, aerosol, foam, cream, liquid and paste.

EXAMPLES

PREPARATION EXAMPLE 1

Preparation of a Melanin Precursor

1. Cloning of a Tyrosinase-Encoding Gene from *Aspergillus oryzae*

A tyrosinase-encoding gene melB from *Aspergillus oryzae* was cloned.

An *Aspergillus oryzae* OSI-1013 strain (FERM P-16528) was implanted to steamed rice. After 1.5 g of koji thus prepared was weighed, it was broken completely in liquid nitrogen. By using "ISOGEN" (product of Nippon Gene), 240 µg of total RNA was extracted. From 120 µg of the total RNA, 1 µg of mRNA was purified using "Oligotex-dT30 <Super>" (product of Takara Bio). A cDNA library of the resulting mRNA was constructed with "SMART cDNA Library Construction Kit" (product of Clontech) and only the melB cDNA was amplified by PCR.

It was confirmed by agarose gel electrophoresis that in the resulting PCR product, only the target band of about 1.8 kbp had been amplified. In addition, it was confirmed as a result of basic sequence analysis that an intron sequence had been deleted correctly from the PCR product 2. Integration in Enzyme Ligation of the cDNA obtained in 1 into an *E. coli* expression vector pET23b (product of Invitrogen), a *Saccharomyces cerevisiae* expression vector (JP-A-2003-265177) or an *Asperigillus oryzae* expression vector (JP-A-2001-224381) under conditions permitting the expression enables abundant expression of tyrosinase in each cell.

In particular, according to the expression example in yeast (in accordance with JP-A-2003-265177), the melB cDNA amplified by PCR was inserted into the SmaI site immediately downstream of the promoter of an expression vector having an SED1 promoter and ADH1 terminator. A melB-cDNA-containing fragment obtained by cleavage at the StuI site within an URA3 marker was purified as an introduction cassette. In this integration, a uracil requiring strain derived from Sake Yeast Kyokai No. 9 ordinarily used for sake brewing was used as the yeast serving as a host.

3. Tyrosinase Activation of Recombinant Yeast and Measurement (3-1) Measurement of Tyrosinase Activity The tyrosinase activity of a cell was measured in the following manner. A portion of the cell was suspended in water, followed by the addition of 0.8 mL of 10 mM L-DOPA (dissolved in 0.005N hydrochloric acid) of 30° C. and 0.1 mL of a 1M sodium phosphate buffer (pH 6.0) to 0.1 mL of the resulting suspension. After reaction at 30° C. for 5 minutes, centrifugal separation was performed at 15,000 rpm for 30 seconds to remove the cell and absorbance at 475 nm, that is, absorption maximum wavelength of DOPA was measured. The amount of the cell was adjusted so that the absorbance of the reaction solution at 475 nm would fall within a range of from 0.1 to 0.3.

(3-2) Activation Treatment of Tyrosinase

The recombinant yeast obtained in 2 was cultured in a conventional manner. The cell was collected by centrifugal separation and washed with distilled water. The cell was suspended in a 50 mM Tris-HCl buffer solution (pH 8.0) containing 2 mM copper sulfate, whose amount was about 10 times the weight of the cell, and the resulting suspension was allowed to stand overnight at 4° C. The cell was collected by centrifugal separation and washed with a 0.1M EDTA solution to remove excess copper ions. The cell thus washed was then suspended in a 0.2M acetate buffer (pH 3.0) and the resulting suspension was allowed to stand at room temperature for 1 hour. The cell thus activated was collected by centrifugal separation as an activated cell.

The tyrosinase activity of the activated cell was measured in accordance with the measuring method described in (3-1), resulting in from 1.9 to 4.4 $U/OD_{600}$. Each transformant strain thus measured was used in the below-described reaction.

4. Accumulation Reaction of Dopachrome

By using the yeast transformant obtained in 3, an accumulation reaction of Dopachrome, which is a melanin precursor, was carried out using L-DOPA as a substrate.

After 7.9 g of L-DOPA was dissolved in 500 mL of 0.03N sulfuric acid, the resulting solution was adjusted to pH 5.5 with 2N potassium hydroxide. The resulting DOPA solution and $2.7 \times 10^5$ U/L (amount so that the activity value of the cell would be $1.35 \times 10^5$ U/L per liter of the reaction solution) obtained in Procedure 3 were charged in a 5-L reaction tank. The reaction was started while adjusting the amount of the solution to be reacted to 2 L.

The reaction temperature was adjusted to 25° C. Since a large amount of oxygen was required just after the initiation of the reaction, the aeration amount and stirring rate were maximized. The solution to be reacted was adjusted to pH 5.5 with sulfuric acid and potassium hydroxide. The reaction was continued for 40 minutes.

The stirring rate and aeration amount in the reaction solution were adjusted with a DO (dissolved oxygen) amount of from 2 to 7 ppm as an indicator. Sampling was performed as needed during the reaction and amounts of Dopachrome and 5,6-dihydroxyindole were determined in the below-described manner. Changes in L-DOPA concentration and melanin precursor concentration in the reaction solution are shown in FIG. 1.

The preparation amount of 5,6-dihydroxyindole-carboxylic acid was very small under these reaction conditions so that the concentration of the precursor was indicated as total of the Dopachrome concentration and 5,6-dihydroxyindole concentration. The Dopachrome concentration upon completion of the reaction is from 3 to 5 times higher than that of the 5,6-dihydroxyindole concentration, though depending on the conditions, which suggests that the melanin precursor is composed mainly of Dopachrome. It is to be noted that the completion of the reaction is judged based on the time when L-DOPA is completely consumed (when the amount of L-DOPA becomes less than the detection limit of the measurement by HPLC). When the amount is not greater than the detection limit, the reaction solution is defined as substantially free of L-DOPA.

In total consideration of a time-dependent change in the melanin precursor concentration, oxygen concentrations which have been recorded, and a time dependent change in the amount of acid or alkali added to keep an adequate pH, the reaction was continued for 40 minutes to completely consume DOPA.

<Quantitative Determination of each Melanin Precursor Component>

Each melanin precursor component was detected and determined using "HPLC Alliance 2695-2996" (product of Waters) under the below-described conditions.

A reverse phase column "Unison UK-C18" (4.6×150 mm) (product of Imtakt) was used for separating the precursor into components; a 1.5% phosphoric acid solution (Solvent A) and a 99.9% methanol (Solvent B) were used as a mobile phase; and a gradient was provided in the mobile phase so that the concentration of Solvent B was 0% at the starting time and 50% after 5 minutes. The flow rate was set at 1.0 mL/min.

A sample to be injected was prepared by adding 100 µL of 20 mM sodium dithionite ($Na_2S_2O_4$) and 890 µL of a 1.5% phosphate ($H_3PO_4$) solution, each per 10 µL of the sample, and the resulting mixture was filtered through a 0.45 µm filter. The sample thus obtained (20 µL) was injected in the column and measurement was performed.

DOPA was detected by monitoring it at an absorbance at 280 nm which was the maximum absorption wavelength. Dopachrome was determined as reduced leucodopachrome (5,6-dihydroxyindoline-2-carboxylic acid) under the above-described measurement conditions. The determination of 5,6-dihydroxyindole was performed based on the standard substance (alkali hydrolysate of 5,6-diacetoxyindole), while 5,6-dihydroxyindole-2-carboxylic acid was determined based on the comparison in a ratio of the peak area at 280 nm. The maximum absorption wavelength of 5,6-dihydroxyindole was 300 nm, while that of 5,6-dihydroxyindolecarboxylic acid was 320 nm.

5. Deproteinization from Melanin Precursor Solution

The melanin precursor solution obtained by the step 4 uses an enzyme cell having a strong cell wall so that it does not contain or hardly contains protein leaked from the cellular debris or cell present in the melanin precursor solution. When it is used as a hair dye, however, a trace amount of protein therein may be an allergen so that protein was removed by ultrafiltration.

As an ultrafiltration apparatus, "Ultrafiltration Module Molsep FS10-FUS0181" (product of Daicen Membrane-systems, cut-off molecular weight: 10000) was employed. The filtrate was provided for SDS-PAGE and silver staining was performed to confirm the absence of protein in the solution. The conventional method of measuring absorbance at 280 nm was not adopted because Dopachrome itself has absorbance in the vicinity of 280 nm and in addition, indole reacts easily with a coloring reagent owing to high reactivity. As a result of silver staining, a band which was presumed to show the presence of protein was not detected after ultrafiltration.

6. Conversion of Dopachrome to 5,6-dihydroxyindole and 5,6-dihydroxyindole-2-carboxylic acid (conversion method of melanin precursor)

The melanin precursor contained in the solution obtained in the step 5 is composed mainly of Dopachrome, that is, 5,6-dihydroxyindoline-2-carboxylic acid. In order to prepare 5,6-dihydroxyindole and 5,6-dihydroxyindole-2-carboxylic acid superior in hair dyeing performance or storage stability as a hair dye, the melanin precursor was subjected to non-enzymatic conversion treatment. For the conversion treatment, pH adjustment, addition of an organic solvent, addition of a phosphate buffer or treatment with metal ion was performed. By any one of these methods, conversion was performed efficiently.

The below-described ratio of the melanin precursor component is indicated by an area ratio determined based on the absorbance at 280 nm.

(6-1) Control of the Composition of the Precursor Solution by pH Adjustment

The composition of the precursor was controlled by adjusting the pH of the melanin precursor solution (composed mainly of Dopachrome) obtained by the step 5. In the absence of oxygen, the solution was stored at 40° C. for 2 hours. Treatment of the solution at a pH from acidic to almost neutral (pH of 5 or greater but less than 8) increased the percentage of 5,6-dihydroxyindole (the percentage of it in the precursor is 50% or greater and 80% or greater under the optimum conditions), while treatment at from pH 8 to 11 increased the percentage of 5,6-dihydroxyindole-2-carboxylic acid. Treatment at pH of from 2 to 4 caused precipitation so that it was not suited for treatment.

(6-2) Use of an Organic Solvent for the Control of the Composition of the Melanin Precursor Solution Ethanol was added to the melanin precursor solution (composed mainly of Dopachrome) obtained in the step 5 so that the amount of ethanol would be 50 vol. % of the total amount. The resulting mixture was then treated at room temperature for 2 hours, whereby Dopachrome was efficiently converted into 5,6-dihydroxyindole (a ratio of 5,6-dihydroxyindole to 5,6-dihydroxyindole-2-carboxylic acid is 10 or greater). Use of methanol, acetone, acetone, 2-propanol or acetonitrile instead of ethanol brought about a similar effect.

2-Aminoethanol was added to the melanin precursor solution obtained in the step 5 so that the amount of ethanol would be 50 vol. % of the total amount. The resulting mixture was treated at room temperature for 2 hours, whereby Dopachrome was efficiently converted into 5,6-dihydroxyindole-2-carboxylic acid (a ratio of 5,6-dihydroxyindole-2-carboxylic acid to 5,6-dihydroxyindole is 5 or greater).

(6-3) Use of a Phosphate Buffer for the Control of the Composition of the Precursor Solution By adding a 1M phosphate buffer to the melanin precursor solution (composed mainly of Dopachrome) obtained in the step described above in 5, a 0.1M phosphate buffer solution of pH 6.0 containing the melanin precursor was prepared. The resulting precursor solution was stored at about −20° C. for 7 days. Dopachrome was efficiently converted into 5,6-dihydroxyindole-2-carboxylic acid by the low-temperature storage of the precursor solution in a phosphate buffer solution containing phosphoric acid as an acid component (a ratio of 5,6-dihydroxyindole-2-carboxylic acid to 5,6-dihydroxyindole is 5 or greater).

(6-4) Use of Sodium Chloride or Sodium Ascorbate for the Control of the Composition of the Precursor Composition Sodium chloride was added to the melanin precursor solution (composed mainly of Dopachrome) obtained in the step 5 to give a final concentration of 2.5%. The resulting mixture was allowed to stand at room temperature for 45 minutes, whereby conversion of Dopachrome to 5,6-dihydroxyindole was accelerated compared with the precursor solution free of sodium chloride. Addition of a sodium ascorbate solution instead of sodium chloride caused a marked amount of 5,6-dihydroxyindole (ratio of 5,6-dihydroxyindole present in the melanin precursor solution: 90%).

(6-5) Use of Copper (II) Salt for the Control of the Composition of the Melanin Precursor Solution Copper sulfate was added to the melanin precursor solution (composed mainly of Dopachrome) obtained in the step 5 to give a final concentration of 1 mM. The resulting mixture was allowed to stand at room temperature for 15 minutes, whereby conversion of Dopachrome to 5,6-dihydroxyindole- 2-carboxylic acid was accelerated (ratio of 5,6-dihydroxyindole-2-carboxylic acid to 5,6-dihydroxyindole: 3 or greater).

7. Concentration of the Melanin Precursor Solution

The melanin precursor solution (Dopachrome, 5,6-dihydroxyindole, 5,6-dihydroxyindole-2-carboxylic acid, and the like) was concentrated in the following manner. For the concentration, a cross-flow type reverse osmotic concentration module (product of Nitto Denko Matex) to be employed for the preparation of pure water from sea water was employed. In this apparatus, between a hermetically closed tank containing the melanin precursor solution and the reverse osmotic concentration module "NTR7410-HG-S4F", the solution was circulated. Pure water produced by this reverse osmotic concentration module was introduced from this module into a transmitted water tank. With the production of pure water, the melanin precursor was concentrated in the tank. Circulation was effected by a pump at a pressure of 2 MPa. About 31 L of the melanin precursor solution obtained by Procedure 5 was concentrated to about 4 L by the operation for about 30 minutes. During the concentration operation, almost no high-molecule melanin was produced in the melanin precursor solution thus transmitted. The 5,6-dihydroxyindole concentration which was used as an index increased from about 9 mM to about 67 mM, showing a considerably high yield.

EXAMPLE 1

1. Preparation of Hair Dye Composition (1) As a melanin precursor composition for hair dye, the following composition was used.

Dopachrome (from about 10 to 15 mM) prepared by use of 20 mM L-DOPA in the oxidation step in which a recombinant yeast (*Saccharomyces cerevisiae*) in which a tyrosinase-encoding gene (melB) derived from *Aspergillus oryzae* which exhibits a tyrosinase activity of from 1.9 to 4.4 U/OD$_{600}$ had been introduced was collected as a supernatant of centrifugal separation (step yield: from about 50 to 65%).

By the treatment in the vicinity of pH 6, ultrafiltration and reverse osmotic membrane concentration, about 1 wt. % of a melanin precursor solution 1 was obtained. The solution contained, as a substance detected as the melanin precursor at 280 nm by HPLC, 5,6-dihydroxyindole in an amount of 90% or greater and 5,6-dihydroxyindole-2-carboxylic acid in an amount of 10% or less. It contained indolins in an amount of 1% or less. L-DOPA used as the starting substance was not detected. It was confirmed by SDS-polyacrylamide electrophoresis that no protein was contained in the solution. By the present process, a melanin precursor composed mainly of 5,6-dihydroxyindole (90% or greater of the melanin precursor content) suited as a hair dye was prepared efficiently.

(2) A hair dye (100 g, invention product 1) having the below-described composition was prepared using 30 g of the melanin precursor solution 1 (containing about 0.3 g of a melanin precursor). In order to avoid mixing of oxygen, it was prepared under anaerobic conditions. The hair dye thus obtained was employed as a stock solution. The stock solution and a propellant (LPG) were both charged in an aerosol container (stock solution:propellant weight ratio=90:10).

| | |
|---|---|
| Melanin precursor solution 1 (about 0.3 g as a melanin precursor) | 30 g |
| Xanthan gum | 0.2 g |
| Aqueous ammonia (28 wt. %) | 0.5 g |
| Ethanol | 10 g |
| "Softanol 90" (product of Nippon Shokubai) | 0.5 g |
| Water | Balance |
| Antioxidant | q.s. |
| total | 100 g |

2. Hair Dyeing Test (Evaluation by a Spectrophotometer)

The hair dye (1 g) obtained in 1 was applied to 1 g of a gray hair tress and dyed at 30° C. for 15 minutes. Then, the resulting hair tress was washed with water, shampooed, rinsed and dried. The above-described operation was performed every 7 days, five times in total. The tress thus dyed was subjected to analysis by a spectrophotometer ("CM-2002", product of Minolta) and evaluated by a color difference (ΔE) calculated in accordance with the following equation:

$$\Delta E = \{(L_1-L_0)^2 + (a_1-a_0)^2 + (b_1-b_0)^2\}^{1/2}$$

wherein, $(L_0, a_0, b_0)$: chromaticity of gray hair tress before dyeing $(L_1, a_1, b_1)$: chromaticity of gray hair tress after dyeing The value ΔE of the gray hair tress was 15 after first dyeing, 28 after third dyeing and 38 after fifth dyeing. The tress became black gradually.

3. Stability

The hair dye was stored at 40° C. for 2 weeks. The main peak determined by HPLC showed almost no change, from which high stability of the hair dye was confirmed.

EXAMPLE 2

Hair Dye Composition (Foam Type)

A hair dye (100 g) was prepared by mixing 5 g of the melanin precursor solution 1 (containing about 0.05 g of the melanin precursor), 0.5 g of "Softanol 90", 0.1 g of xanthan gum, 0.3 g of stearyl trimethylammonium chloride, 0.01 g of polyoxyethylene·methylpolysiloxane copolymer, 10 g of ethanol and balance of water. The hair dye composition was prepared under the anaerobic conditions in order to avoid mixing of oxygen. The hair dye thus obtained was used as a stock solution. The stock solution and a propellant (LPG) were both charged together in an aerosol container (stock solution:propellant weight ratio=90:10)

What is claimed is:

1. A method for the production of an air-oxidative type hair dye composition that comprises a melanin precursor, said method comprising (a) converting, in a reaction solution, tyrosine, or a derivative thereof, into a melanin precursor, by using a catechol oxidase enzyme of a fungus to catalyze the oxidation of said tyrosine or said derivative thereof into said melanin precursor, or by using cells that express said enzyme, wherein said fungus belongs to a genus selected from the group consisting of *Aspergillus, Neurospora, Rhizomucor, Trichoderma*, and *Penicillium*, (b) removing said enzyme or said cells from said reaction solution, and, (c) after removing said enzyme or said cells, incorporating said melanin precursor into a hair dye composition.

2. The method according to claim 1, wherein said melanin precursor comprises 5,6-dihydroxyindole and/or 5,6-dihydroxyinole-2-carboxylic acid and after the converting of part (a), the reaction solution that contains said melanin precursor is treated to raise the concentration of 5,6-dihydroxyindole and/or 5,6-dihydroxyindole-2-carboxylic acid.

3. The method according to claim 2, wherein the concentration of said 5,6-dihydroxyindole and/or 5,6-dihydroxyindole-2-carboxylic acid is raised by one or more treatments selected from the group consisting of (i) pH adjustment, (ii) addition of a water-soluble organic solvent, (iii) addition of an inorganic salt, (iv) treatment with a buffer, and (v) addition of an antioxidant.

4. The method of claim 1, wherein said catechol oxidase is a tyrosinase and wherein said tyrosinase is substantially the same as the tyrosinase encoded by the *Aspergillus oryzae* tyrosinase-encoding gene melB, the *Aspergillus oryzae* tyrosinase-encoding gene melD or the *Aspergillus oryzae* tyrosinase-encoding gene melO.

5. The method according to claim 1, wherein said method uses said cells that express said catechol oxidase enzyme and wherein said cells are *Escherichia coli*, yeast of fungal cells.

6. The method according to claim 1, wherein the substrate for catechol oxidase comprises L-3-(3,4-dihydroxyphenyl)alanine(L-DOPA), and wherein the concentration of 3-(3,4-dihydroxyphenyl)alanine(DOPA) is 15 mM or greater upon initiation of said converting of part (a) and 0.1 mM or less upon completion of said converting of part (a).

7. The method according to claim 1, wherein said melanin precursor comprises 5,6-dihydroxyindole and wherein the percentage of 5,6-dihydroxyindole in the melanin precursor is 60% or greater in terms of an area ratio of absorbance at 280 nm.

8. The method according to claim 1 wherein said melanin precursor is prepared by using a 3-(3,4-dihydroxyphenyl)alanine(DOPA) ester or a tyrosine ester as the substrate for said catechol oxidase.

9. The method according to claim 1 wherein said hair dye composition has a pH of from 6 to 11.

10. The method according to claim 1, wherein 3-(3,4-dihydroxyphenyl)alanine(DOPA) or 3,4-dihydroxyphenethylamine (Dopamine) is used as the starting substance or an intermediate and wherein said hair dye composition is essentially free of said 3-(3,4-dihydroxyphenyl)alanine(DOPA) or 3,4-dihydroxyphenethylamine (Dopamin).

11. A method for the production of melanin precursor, said method comprising
  (a) converting, in a reaction solution, tyrosine, or a derivative thereof, into a melanin precursor, by using a catechol oxidase enzyme of a fungus to catalyze the oxidation of said tyrosine or said derivative thereof into said melanin precursor, or by using cells that express said enzyme, wherein said fungus belongs to a genus selected from the group consisting of *Aspergillus, Neurospora, Rhizomucor, Trichoderma*, and *Penicillium*
  (b) removing said enzyme or said cells from said reaction solution, and
  (c) after part (a), or after part (b), treating said reaction solution to raise the concentration of 5,6-dihydroxyindole and/or 5,6-dihydroxyindole-2-carboxylic acid,
  wherein said melanin precursor comprises Dopachrome, 5,6-dihydroxyindole, and 5,6-dihydroxyindole-2-carboxylic acid.

12. The method according to claim 11, wherein the concentration of said 5,6-dihydroxyindole and/or 5,6-dihydroxyindole-2-carboxylic acid is raised by one or more treatments selected from the group consisting of (i) pH adjustment, (ii) addition of a water-soluble organic solvent, (iii) addition of an inorganic salt, (iv) treatment with a buffer, and (v) addition of an antioxidant.

13. The method of claim 11, wherein said catechol oxidase is a tyrosinase and wherein said tyrosinase substantially the same as the tyrosinase encoded by the *Aspergillus oryzae* tyrosinase-encoding gene melB, the *Aspergillus oryzae* tyrosinase-encoding gene melD or the *Aspergillus oryzae* tyrosinase-encoding gene melO.

14. The method according to claim 11, wherein said method uses said cells that express said catechol oxidase enzyme and wherein said cell is a *Escherichia coli*, yeast or fungal cell.

15. The method according to claim 11, wherein the substrate for catechol oxidase comprises L-3-(3,4-dihydroxyphenyl)alanine(L-DOPA), and wherein the concentration of L-3-(3,4-dihydroxyphenyl)alanine(L-DOPA) is 15 mM or greater upon initiation of said converting of part (a) and 0.1 mM or less upon completion of said converting of part (a).

16. The method according to claim 11, wherein the melanin precursor comprises 5,6-dihydroxyindole and wherein the percentage of 5,6-dihydroxyindole in the melanin precursor is 60% or greater in terms of an area ratio of absorbance at 280 nm.

17. The method according to claim 11, wherein said melanin precursor is prepared by using a 3-(3,4-dihydroxyphenyl)alanine(DOPA) ester or a tyrosine ester as the substrate for said catechol oxidase.

18. The method according to claim 11, wherein said hair dye composition has a pH of from 6 to 11.

19. The method according to claim 11, wherein 3-(3,4-dihydroxyphenyl)alanine(DOPA) or 3,4-dihydroxyphenethylamine(Dopamine) is used as the starting substance or an intermediate.

* * * * *